(12) United States Patent
Ebejer et al.

(10) Patent No.: US 12,070,307 B2
(45) Date of Patent: Aug. 27, 2024

(54) ELECTRICALLY FUNCTIONAL POLYMER MICRONEEDLE ARRAY

(71) Applicant: International Business Machines Corporation, Armonk, NY (US)

(72) Inventors: Neil Ebejer, Lausanne (CH); Ute Drechsler, Rueschlikon (CH); Patrick Ruch, Pratval (CH)

(73) Assignee: International Business Machines Corporation, Armonk, NY (US)

( * ) Notice: Subject to any disclaimer, the term of this patent is extended or adjusted under 35 U.S.C. 154(b) by 785 days.

(21) Appl. No.: 17/132,165

(22) Filed: Dec. 23, 2020

(65) Prior Publication Data
US 2021/0106259 A1 Apr. 15, 2021

Related U.S. Application Data (62) Division of application No. 15/980,917, filed on May 16, 2018, now Pat. No. 10,980,448.

(51) Int. Cl.
*A61B 5/145* (2006.01)
*A61B 5/00* (2006.01)
(Continued)

(52) U.S. Cl.
CPC ........ *A61B 5/14514* (2013.01); *A61B 5/1473* (2013.01); *A61B 5/685* (2013.01);
(Continued)

(58) Field of Classification Search
None
See application file for complete search history.

(56) References Cited

U.S. PATENT DOCUMENTS

| | | |
|---|---|---|
| 6,379,324 B1 | 4/2002 | Gartstein et al. |
| 7,060,192 B2 | 6/2006 | Yuzhakov et al. |

(Continued)

FOREIGN PATENT DOCUMENTS

| | | |
|---|---|---|
| JP | 2003501163 A | 1/2003 |
| JP | 2004526581 A | 9/2004 |

(Continued)

OTHER PUBLICATIONS

Xiang, Z., et al., "A flexible three-dimensional electrode mesh: An enabling technology for wireless brain-computer interface prostheses", Microsystems & Nanoengineering (2016), Oct. 17, 2015, revised Feb. 21, 2016, accepted Mar. 1, 2016, Published online May 23, 2016, 8 pages, 2, 16012.

(Continued)

*Primary Examiner* — Feifei Yeung Lopez
(74) *Attorney, Agent, or Firm* — Scully, Scott, Murphy & Presser, P.C.; Daniel P. Morris (57) ABSTRACT

A sensor device, such as a biosensor, may comprise a polymer substrate, which is structured so as to form sets of microneedles and respective vias. The microneedles extend, each, from a base surface of the substrate. Each of the vias extends through a thickness of the substrate, thereby forming a corresponding set of apertures on the base surface. Each of the apertures is adjacent to a respective one of the microneedles. The device further may comprise two or more electrodes, these including a sensing electrode and a reference electrode. Each electrode may comprise an electrically conductive material layer that coats a region of the substrate, so as to coat at least some of the microneedles and neighboring portions of said base surface. Related devices, apparatuses, and methods of fabrication and use of such devices may be provided.

14 Claims, 5 Drawing Sheets

(51) Int. Cl.
  *A61B 5/1473* (2006.01)
  *H05K 3/00* (2006.01)
  *A61B 10/00* (2006.01)

(52) U.S. Cl.
  CPC ...... *H05K 3/0014* (2013.01); *A61B 2010/008* (2013.01); *A61B 2562/125* (2013.01); *B81C 2201/0101* (2013.01); *B81C 2201/0108* (2013.01); *B81C 2201/013* (2013.01); *B81C 2201/0147* (2013.01); *B81C 2201/056* (2013.01)

(56) References Cited

U.S. PATENT DOCUMENTS

| | | | |
|---|---|---|---|
| 7,344,499 | B1 | 3/2008 | Prausnitz et al. |
| 8,865,288 | B2 | 10/2014 | Bhandari et al. |
| 9,330,820 | B2 | 5/2016 | Allen et al. |
| 9,675,790 | B2 | 6/2017 | Stoeber et al. |
| 2002/0168290 | A1 | 11/2002 | Yuzhakov et al. |
| 2005/0011858 | A1 | 1/2005 | Kuo et al. |
| 2007/0114524 | A1 | 5/2007 | Oh et al. |
| 2007/0179428 | A1 | 8/2007 | Kralick et al. |
| 2009/0099502 | A1* | 4/2009 | Tokumoto ......... A61M 37/0015 604/21 |
| 2009/0259118 | A1 | 10/2009 | Feldman et al. |
| 2013/0306356 | A1 | 11/2013 | Allen et al. |
| 2015/0208984 | A1 | 7/2015 | Huang |
| 2016/0027867 | A1 | 1/2016 | Matsushita |
| 2016/0278672 | A1 | 9/2016 | Cho et al. |
| 2017/0007813 | A1 | 1/2017 | Negi et al. |

FOREIGN PATENT DOCUMENTS

| | | | |
|---|---|---|---|
| JP | 2006516226 | A | 6/2006 |
| WO | 00/74763 | A2 | 12/2000 |
| WO | 2000074766 | A1 | 12/2000 |
| WO | 2002072189 | A2 | 9/2002 |
| WO | 2004062899 | A2 | 7/2004 |
| WO | 2013/058879 | A2 | 4/2013 |

OTHER PUBLICATIONS

Barrett, C., et al., "Development of Low Cost Rapid Fabrication of Sharp Polymer Microneedles for In Vivo Glucose Biosensing Applications", ECS Journal of Solid State Science and Technology (2015), Manuscript submitted Jun. 5, 2015, Revised manuscript received Aug. 17, 2015, Published Aug. 27, 2015, pp. S3053-S3058, 4 (10).

Ceyssens, F., et al., "Fabrication process for tall, sharp, hollow, high aspect ratio polymer microneedles on a platform", Journal of Micromechanics and Microengineering, in final form Apr. 30, 2013, Published Jun. 12, 2013, 12 pages, vol. 23, No. 7.

International Search Report dated Aug. 7, 2019, together with Written Opinion received in International Application No. PCT/IB2019/052892, 10 pages.

List of IBM Patents or Patent Applications Treated as Related, dated Dec. 23, 2020, 2 pages.

United Kingdom Examination Report dated Oct. 28, 2021 issued in GB2018033.7, 4 pages.

Notice of Reasons for Refusal dated Aug. 3, 2022 received in Japanese Patent Application No. 2020-552314, 17 pages.

First Office Action dated May 15, 2024 issued in Chinese Application No. 201980028644.2, 20 pages.

* cited by examiner

ELECTRICALLY FUNCTIONAL POLYMER MICRONEEDLE ARRAY

BACKGROUND

The present disclosure relates in general to the field of sensor devices, in particular biosensors, having microneedles and electrodes for probing a fluid, in particular a physiological fluid. It is further related to related methods of fabrication and operation.

A sensor is a device or a module used to detect events or changes in properties (e.g., chemical, physical) of the sensor or the environment of the sensor. The signals sensed are typically processed by electronics it includes or it connects to, e.g., remotely. As an important class of sensors, biosensors make it possible to obtain data about the physiological state of a person and, as such, enable a range of health and medical applications.

Being able to selectively detect biomarkers would make it possible to more efficiently reach useful information without resorting to heavy data manipulation. The current technology used in biosensors is trending towards sweat sensing. Sweat is indeed an interesting medium to probe. However, an inherent drawback of sweat is that it requires substantial physical activity to generate an adequate sample volume, unless sweat inducing drugs are relied on, which often is unsuitable.

Microneedle electrode arrays are known, which overcome this limitation by probing interstitial fluid. However, currently known devices are either painful to the end user, difficult to apply and/or inconvenient to wear for extended periods of time. In addition, the designs of such devices may not be suitable for mass-fabrication.

The paper "Development of Low Cost Rapid Fabrication of Sharp Polymer Microneedles for In Vivo Glucose Biosensing Applications" (C. Barrett, K. Dawson, C. O'Mahony and A. O'Riordan, ECS Journal of Solid State Science and Technology, 4 (10) S3053-S3058 (2015)) describes the fabrication of a minimally invasive transdermal sensor for direct in vivo detection of glucose in interstitial fluid, based on a dual molding technique using a PDMS polymer. However, the fabrication method described in this paper is perceived by the present Inventors as not being easily scalable. Moreover, the process used for pre-patterning the electrode materials is quite complex to implement in production.

SUMMARY

According to a first aspect, the present invention is embodied as a sensor device, such as a biosensor. The device comprises a polymer substrate, which is structured so as to form sets of microneedles and respective vias. The microneedles extend, each, from a base surface of the substrate. Each of the vias extends through a thickness of the substrate, thereby forming a corresponding set of apertures on the base surface. Each of the apertures is adjacent (i.e., next) to a respective one of the microneedles. The device further comprises two or more electrodes, these including a sensing electrode and a reference electrode. Each electrode comprises an electrically conductive material layer that coats a region of the substrate, so as to coat at least some of the microneedles and neighboring portions of said base surface.

Providing the vias and corresponding apertures adjacent to the needles preserves the mechanical stability of the structured polymer substrate and simplifies the fabrication process, especially when compared, e.g., to solutions relying on hollow needles. Such a design further eases the release of the substrate during a liftoff process step, as involved in preferred fabrication methods described herein. Moreover, the present approach makes it possible to coat any region of the polymer substrate, including inner conduits of the vias. All in all, the above design makes it possible to easily fabricate sensor devices such as biosensors with fitting properties. Such devices can for instance be used for in vivo detection of interstitial fluids, or for food or drug testing, amongst other examples.

In preferred embodiments as described herein, each of the microneedles has one (and preferably only one) facet that is essentially perpendicular to the base surface of the substrate, which results in sharper needles in practice. For instance, the apertures of the vias may, each, be adjacent to and at a basis of the perpendicular facet of a respective one of the microneedles. The standard deviation of angles between such perpendicular facets and the base surface of the substrate is, e.g., less than 4°.

Preferably, the average height of the microneedles is less than or equal to 400 µm. This height is measured perpendicular to and from the base surface of the substrate. On the other hand, this average height typically need be made larger than or equal to 30 µm, or even 100 µm, in order to be able to suitably probe the sample.

In embodiments, the microneedles form an array of microneedles, whereby the microneedles are distributed on the base surface of the polymer substrate according to a 2D lattice. The average, first-neighbor distance between apices of the microneedles in the array shall preferably be less than or equal to 3 mm in practice. Each first-neighbor distance is measured parallel to said base surface of the polymer substrate. Advantageously though, a condition can be imposed between the first-neighbor distance and the needle height. Namely, the average, first-neighbor distance is preferably made larger than or equal to three times the average height of the microneedles, where this average height is between 30 µm and 400 µm.

Preferably, each of the electrically conductive material layers of the electrodes coats respective, non-overlapping portions of the base surface of the substrate, e.g., around the apertures, and so as to coat the microneedle facets too.

In embodiments, the sensor device further includes one or more additional electrodes. Each additional electrode comprises an electrically conductive material layer that partly coats a respective portion of the base surface of the substrate (this including, e.g., facets of microneedles arranged on such a portion), wherein said respective portion does not overlap with any of the portions of the base surface coated by the material layers of the other electrodes of the device.

The material layers of the electrode may notably be structured so as to coat complementary portions of the base surface of the polymer substrate, which complementary portions may for instance be arranged in distinct sectors of the base surface of the substrate.

Moreover, one or each of the electrodes is preferably structured so as to electrically connect opposite sides of the substrate (said base surface being on one of said opposite sides), to ease connection to/from the electrodes.

In embodiments, the polymer substrate comprises a photosensitive polymer, such as a SU-8 polymer, though other negative-tone photoresists may be used, for example.

The sensor device shall typically include a readout electronic unit. Yet, the device may, in variants, be provided as a kit of parts, where the readout unit is mechanically attachable and thereby electrically connectable to a sensing part of the device. In other variants, connection wires may be used. The readout electronic unit may, in all cases, comprise a housing and electronics encapsulated in the housing, wherein the electronics and the housing are configured such that the electronics can be set in electric communication with the electrodes. The electronics are otherwise configured to read signals obtained from the electrodes, in operation of the sensor device.

According to another aspect, the invention is embodied as a method of fabrication of a sensor device. This method essentially revolves around patterning and structuring a polymer substrate, so as to form sets of microneedles and vias, as well as electrodes coating regions of the substrate, as in sensor devices described above.

Preferably though, and according to a preferred aspect, the invention is embodied as a method of fabrication, wherein electrically conductive material layers are patterned onto a sacrificial layer that coats a mold structured so as to form an inverse pattern. In fact, the electrically conductive material layers and the sacrificial layer can advantageously be patterned as a stack that altogether coats the structured mold. Then, the polymer substrate is complementarily patterned onto the electrically conductive material layers to form a set of microneedles according to said inverse pattern. This way, each microneedle extends from a base surface of the substrate. The polymer substrate is otherwise structured so as to exhibit a set of vias that extend, each, through a thickness of the polymer substrate, thereby forming a corresponding set of apertures on said base surface of the polymer substrate. In addition, each of the apertures is adjacent to a respective one of the microneedles formed. Finally, the sacrificial layer is removed to release the polymer substrate with the electrically conductive material layers formed thereon. Eventually, a sensor device is obtained, which has electrodes formed by said material layers. Thanks to a suitably defined electrode patterning, the electrically conductive material layers coat regions of the substrate, so as to coat at least some of the microneedles and neighboring portions of the base surface of the substrate.

In embodiments, this fabrication method further comprises a series of initial steps (prior to patterning the electrically conductive material layers onto the sacrificial), which aim at obtaining the desired inverse pattern and enabling an easy liftoff process. That is, an oxidized silicon substrate is first obtained, wherein an oxide layer is on top of the substrate. Then, the oxide layer is patterned to form openings through residual portions of the oxide layer. Next, the silicon substrate is etched through the openings formed to obtain said inverse pattern, whereby cavities are created, which are shaped complementarily to the microneedles to be subsequently obtained. Said residual portions of the oxide layer are subsequently removed to obtain the structured mold. Finally, the sacrificial layer is deposited on the structured mold, so as to allow a subsequent patterning of the electrode layers meant to remain on the substrate after the release. Note, however, that the sacrificial layer is preferably deposited, altogether with other metal layers, as a metal stack on the mold.

Preferably, the patterning of the polymer substrate includes selectively exposing the polymer to a radiation source, which makes it possible to increase the sharpness of the needles in practice, as Inventors observed.

In preferred embodiments, the above steps of patterning the material layers, complementarily patterning the polymer substrate and removing the sacrificial layer are implemented on a wafer scale. In that case, after the release, the wafer-scale polymer substrate is split in order to obtain several sensor devices, each comprising a structured polymer substrate with respective electrodes and sets of microneedles, vias and apertures, as described above.

According to a final aspect, the invention is embodied as a method of analysis of a fluid. Basically, this method relies on a sensor device as evoked above, which is applied on a body (e.g., food or drug product, a part of a human body or an animal, etc.). The polymer substrate is applied onto this body, e.g., so as for the microneedles to slightly penetrate into this body. This allows a fluid from the body to contact one or more surface of the electrodes that are exposed to the body. Signals obtained from the electrodes are subsequently read, e.g., thanks to a readout electronic unit such as evoked above.

Devices, apparatuses, methods of fabrication and use of sensor devices such as described above, which embody the present invention, will now be described by way of non-limiting examples and in reference to the accompanying drawings.

BRIEF DESCRIPTION OF SEVERAL VIEWS OF THE DRAWINGS

The accompanying figures, where like reference numerals refer to identical or functionally similar elements throughout the separate views, and which together with the detailed description below are incorporated in and form part of the present specification, serve to further illustrate various embodiments and to explain various principles and advantages all in accordance with the present disclosure, in which.

The accompanying drawings show simplified representations of devices or parts thereof, as involved in embodiments. Technical features depicted in the drawings are not necessarily to scale. Similar or functionally similar elements in the figures have been allocated the same numeral references, unless otherwise indicated.

DETAILED DESCRIPTION OF EMBODIMENTS OF THE INVENTION

In reference to FIGS. 1-8, an aspect of the invention is first described, which concerns a sensor device 1. The device 1 (FIG. 1) essentially comprises a structured polymer substrate 10 (FIGS. 2-3 and 7-8), which can accommodate a number of variants 10a-10c (FIGS. 4-6), onto which electrodes are coated to sense fluids, as explained in the following.

As illustrated in FIGS. 2-3 and 7-8, the polymer substrate 10 is structured so as to form: (i) a set of microneedles 16; as well as (ii) a set of respective vias 17. The microneedles 16 extend, each, from a base surface S of the substrate 10. The microneedles 16 are not hollow needles; they instead compare to sharp solid rods or tips. The vias 17 extend, each, through a thickness of the substrate 10. Each via 17 forms a corresponding aperture 18 on the base surface S. Each aperture 18 is adjacent to a respective one of the microneedles 16. That is, each aperture 18 is next to and, preferably, in the immediate vicinity of a respective microneedle: apertures are arranged sufficiently far from the needle locations, such that the microneedles 16 are not hollow needles.

Figure 2:
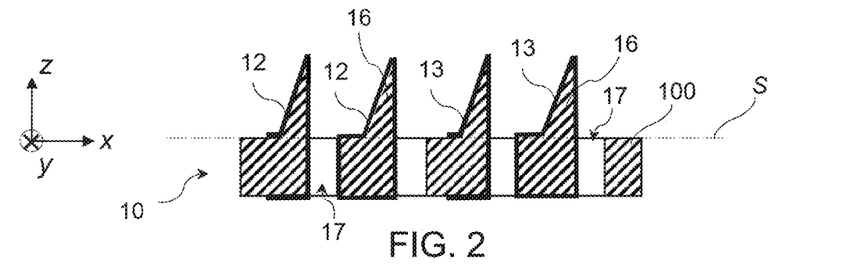
FIG. 2 is a 2D cross-sectional view of a sensing part of a sensor device similar to that of FIG. 1, showing microneedles and vias formed in a polymer substrate, according to embodiments. The cross-sectional view is taken along the cutting-plane A-A shown in FIG. 3.
Figure 3:
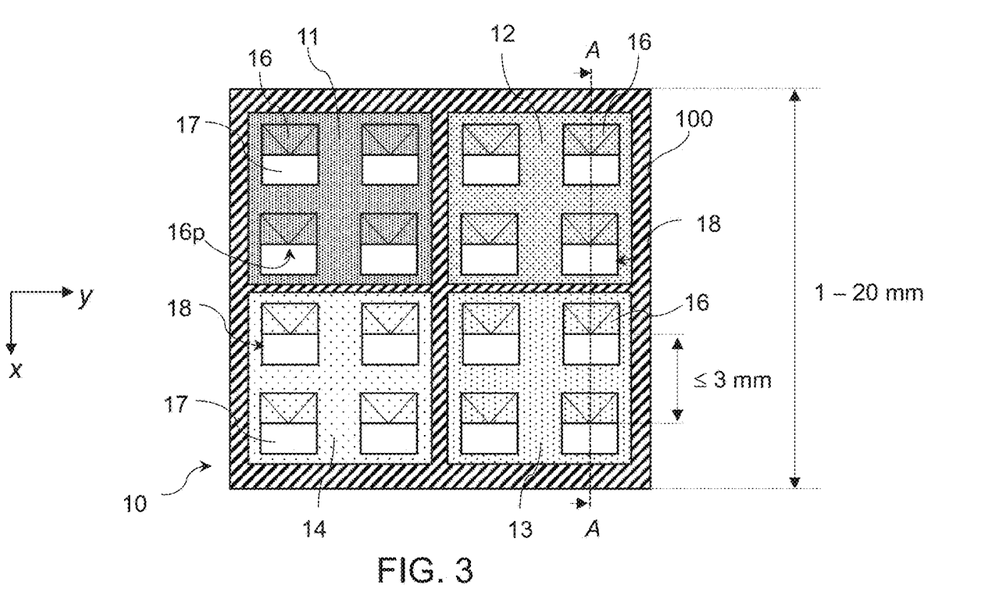
FIG. 3 is a top view corresponding to the cross-section of FIG. 2, showing a sensor device with four electrodes formed on top of the polymer substrate and arranged in quadrants, as in embodiments.

The device 1 further includes two or more electrodes 11-15a. Electrodes include at least a sensing electrode and a reference electrode. Each electrode 11-15a comprises an electrically conductive material layer that coats a region of the substrate 10. In fact, each electrode 11-15a coats at least some of the microneedles 16, as well as neighboring portions of the base surface S, as illustrated in FIGS. 2 and 3. In variants, three or more electrodes 11-15a may similarly be formed on the substrate 10.

As further shown in FIGS. 2-7, the electrically conductive material layers of the electrodes shall preferably coat regions of the substrate 10 around the apertures 18, so as not to obstruct the vias 17. That is, apertures are present in the electrode layers, which coincide with apertures 18. In that case, the free apertures 18 and vias 17 form access ports, which can notably be used for optical access (insertion depth), or for introducing an anti-bacterial and/or an inflammatory gel, or still for evacuating sweat (as assumed in FIG. 7), for example.

In variants, however, it may be desirable to have a free-standing membrane remaining above the apertures 18, for example to prevent evacuation of liquid from the region of insertion or to selectively filter certain liquid components. In such variants, a polymer membrane may be applied as a layer of the stack 70, for example by means of spin-coating or electrodeposition, so as to maintain said polymer membrane suspended above the apertures 18 in the final device structure. The polymer membrane may further be made impermeable to moisture, for instance, by electrodepositing a sufficient thickness, e.g., larger than 5 µm, of a suitable polymer (polypyrrole, polyaniline, etc.). In contrast, a polymer membrane which is permeable to selected molecules, e.g. caffeine, may be obtained by electrodepositing a matrix such as a molecularly imprinted polypyrrole. Such selective membranes may prove useful in practice, e.g., when it is desirable to evacuate certain analytes from the region of insertion or, conversely, to introduce certain compounds into the region of insertion through said polymer membrane at a defined rate and purity.

Providing the vias 17 and corresponding apertures 18 adjacent to the needles preserves the mechanical stability of the structured polymer substrate 10, especially when compared, e.g., to solutions relying on hollow needles. Such a design further happens to ease the release of the substrate 10 during the liftoff process step, as involved in preferred fabrication methods described below. All in all, the present approach makes it possible to easily fabricate a sensor device having fitting properties.

Figure 7:
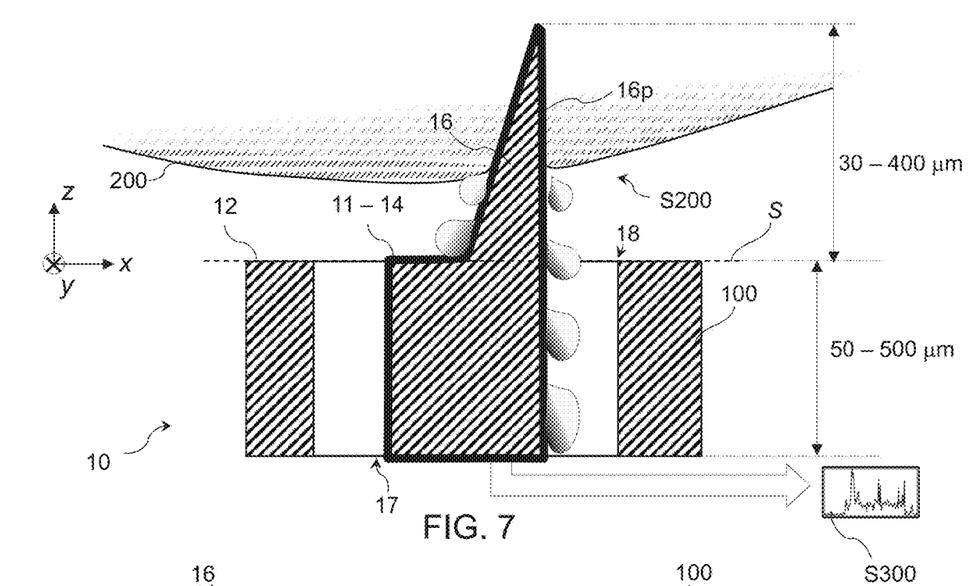
FIG. 7 is a magnified portion of the 2D cross-sectional view of FIG. 2, which further illustrates the sensor device in operation, as in embodiments.
Figure 8:
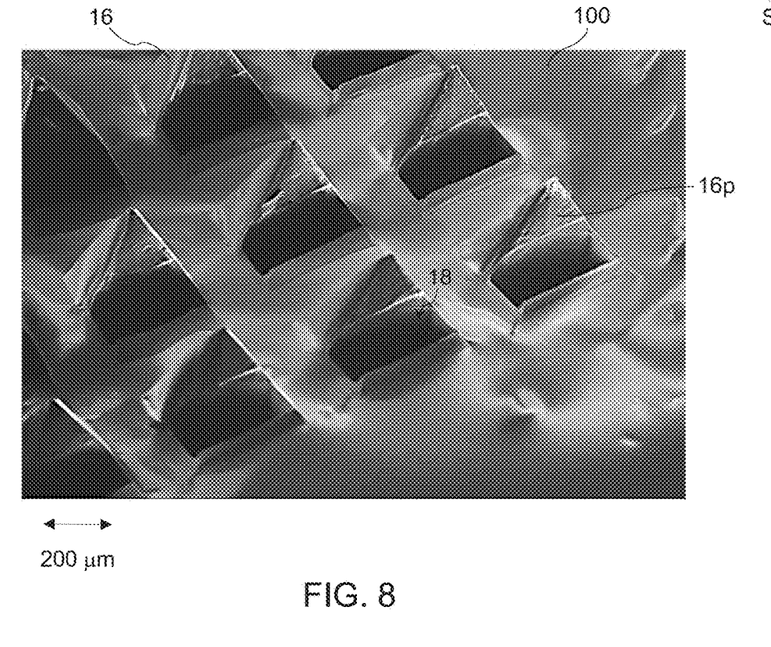
FIG. 8 is a scanning electron microscope image of the structured polymer surface of an actual sensor device, according to embodiments, which device is otherwise similar to the device shown in FIG. 3.

Referring more specifically to FIGS. 2, 7: in embodiments, each of the microneedles 16 has one facet 16p that is essentially perpendicular to the base surface S of the substrate 10. Each microneedle 16 preferably has only one such perpendicular facet 16p. Imposing perpendicular facets 16p in the fabrication of the needles results in sharper needles in practice. Note, the terminology "perpendicular facet" as used herein means that a facet 16p forms an angle with the base surface S (or equivalently with the average plane of the substrate 10, which is an essentially planar object), where this angle is between 82° and 98°, and preferably between 87° and 93°. In fact, fabrication methods as disclosed herein indeed allow fairly perpendicular facets 16p to be obtained, i.e., forming an angle of 90° with the substrate 10 with a standard dispersion that typically is less than 4°. That is, angles formed by the perpendicular facets 16p are essentially equal to 90±2°.

In embodiments, the apertures 18 of the vias 17 are, each, adjacent to and at the basis of the perpendicular facet 16p of a respective one of the microneedles 16, as illustrated in FIGS. 2-8. This makes it possible to easily evacuate sweat or other fluids, or to introduce a gel or fluid in the vicinity of a needle, yet without compromising the integrity of the needle-structured polymer. The aperture shall typically have a rectangular shape, or at least exhibit one side, whose length is substantially equal to the width of the perpendicular facets. Still, other apertures shapes such as semi-circular apertures may easily be processed.

Referring more particularly to FIG. 7, the average height of the microneedles 16 is preferably less than or equal to 400 µm. The heights of the microneedles are measured perpendicular to and from the base surface S. I.e., this height is the distance from the apex of a needle 16 to the basis plane surface S of the substrate 10. On the other hand, this average height typically need be made larger than or equal to 30 µm, or even 100 µm, so as to ease the sample collection. In addition, fabrication constraints and tolerances may typically impose a minimal height to the needles.

Figure 4:
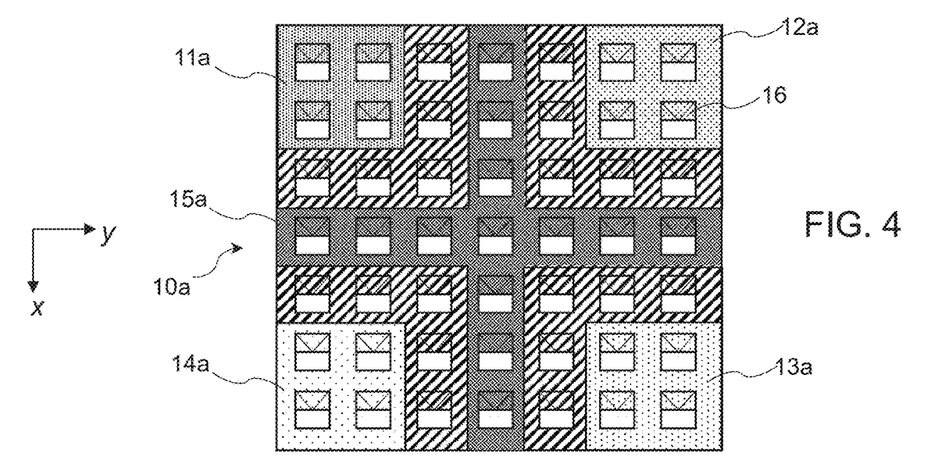
FIGS. 4-6 show top views of devices according to variants to FIG. 3, wherein the electrodes formed on top of the polymer substrate have different arrangements.
Figure 5:
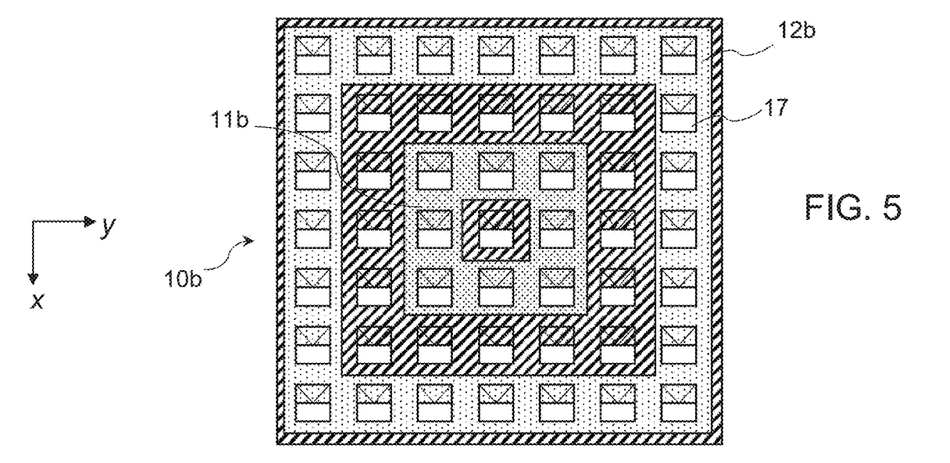
Figure 6:
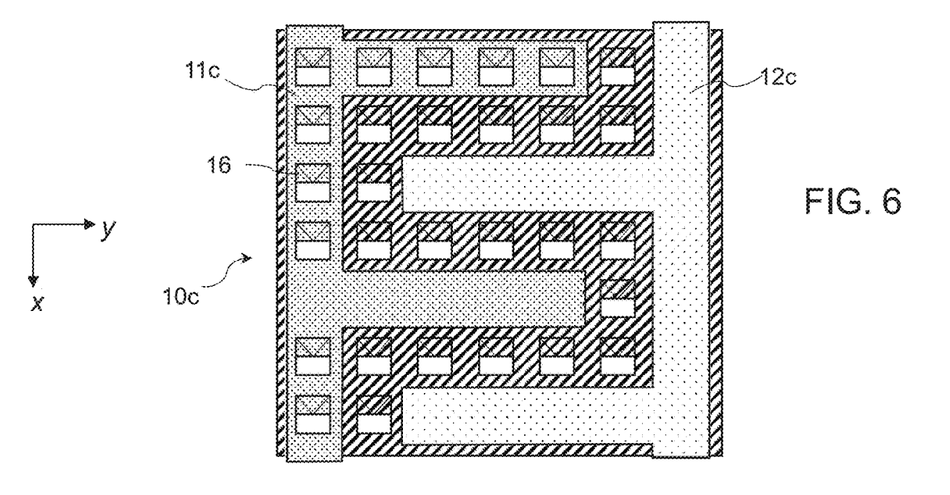

Referring now to the top view of FIGS. 3-6, the microneedles 16 may typically form an array of microneedles 16. I.e., the microneedles 16 are preferably distributed on the base surface S according to a 2D lattice. Typically, a highly symmetric pattern (e.g., such as a square or hexagonal lattice) is relied on, though other lattice patterns (e.g., rhombic or rectangular) can be contemplated. Still, needles need not systematically be formed at each lattice position, as seen in FIG. 6, though they preferably do in typical applications, which incidentally simplifies the design and fabrication process.

In the examples of FIGS. 3-5, the average, first-neighbor distance between apices of the microneedles 16 is assumed to be less than or equal to 3 mm. Such an upper boundary results in a lower boundary for the areal density of needles, which is adequate for typical biosensing applications. Each first-neighbor distance is here measured parallel to the base surface S. This distance corresponds, in the examples of FIGS. 3-5, to a lattice step of the 2D lattice (square). In addition, one may impose the first-neighbor distance to be larger than or equal to three times the average height of the microneedles 16, which average height is preferably larger than or equal to 30 µm and less than or equal to 400 µm, as noted earlier. Indeed, as the present Inventors have concluded from the various tests they performed, imposing this condition allows, given a reasonable average needle height, a sufficiently sparse array 10, 10a-10c of needles, which is most suitable for biosensing applications, e.g., for probing interstitial fluid. That is, the resulting designs happen to be sufficiently painless to a user who wears the sensor for an extended period of time, while still allowing sufficient quantities of fluids to be probed in practice. As a result, the average (first-neighbor) distance between apices of the needles will typically be larger than 90 µm (though it can reach the mm range). It preferably is larger than or equal to 360 µm, assuming 120 µm high needles.

In terms of overall dimensions, the thickness of the polymer substrate 10, 10a-10c (i.e., apart from the needles) shall typically be between 50 µm and 500 µm. The edge lengths of the polymer substrate may for instance be between 1 mm and 20 mm. The overall shape of the substrate 10 may notably be rectangular, circular, or have any shape adapted to the sensing application contemplated (e.g., to favorably conform to the skin surface on which it is meant to be placed).

In terms of materials, the polymer material used to structure the substrate 10, 10a-10c preferably comprises a photosensitive polymer, such as a SU-8 polymer. In variants, other negative-tone photoresists such as the so-called KMPR® or UVN®30 polymers, can be contemplated. Still, many other polymeric materials may be contemplated. Moreover, each electrode 11-15a typically consist of a metal layer 71-75 (or more likely a stack 70 of metal layers, see FIG. 10), whose thickness is typically between 5 nm and 500 nm (per layer). In preferred embodiments, such a stack 70 includes gold 72, 74 (100 nm) and titanium 71, 75 (10 nm), where a gold layer 75 forms the exposed surface, while the titanium layer(s) serve(s) to promote the adhesion between gold and the polymer material used for structuring the substrate 10, 10a-10c. Beside gold, other metals of interest for sensing applications include platinum and silver. The metals may be further treated, for example by electrochemical or thermal oxidation or chemical chlorination, in order to obtain sensing materials of interest. Further materials such as ceramics (e.g., TiN, $RuO_2$, $IrO_x$) or polymers (e.g., membranes for ion-selective electrodes, or ISEs), which are known per se, may also be deposited onto the microneedles 16 as part of the fabrication process or after the release of the polymer, as explained later in reference to preferred fabrication methods.

As illustrated in FIGS. 3-6, each of the electrically conductive material layers of the electrodes 11-15a may be deposited so as to coat respective, non-overlapping portions of the base surface S of the structured substrate 10, 10a-10c, e.g., around the apertures 18, and so as to coat facets of the microneedles 16 too (including the perpendicular facets 16p).

Beyond a sensing electrode and a reference electrode, the sensor device 1 may further include one or more additional electrodes. For instance, in embodiments such as illustrated in FIGS. 3-6, the sensor device 1 further includes two or three additional electrodes 13, 14, 15a. Similarly to electrodes 11, 12, such additional electrodes comprise, each, one or more electrically conductive material layers, this including a layer that partly coats a respective portion of the base surface S of the substrate. This respective portion does not overlap with any of the portions of the base surface S that are otherwise coated by material layers of the other electrodes 11, 12, etc., of the device. I.e. all electrodes are arranged on distinct portions of the base surface S, so as not to be in direct electrical contact.

For example, the material layers used for the electrodes may be structured so as to coat complementary portions of the base surface S. Such complementary portions may be more or less compact, as illustrated in FIGS. 3-5, or, on the contrary, form an intermingled or interdigitated pattern, as in FIG. 6. In all cases, the conductive coatings may be laterally separated from each other on the base surface S, so as not to be in direct electrical contact with one another. In variants, an electrical barrier may explicitly be deposited on the surface S to prevent direct electrical contacts. In other variants, a trench may be opened a posteriori, after the deposition of the electrode material layers, e.g., so as to make it possible to customize the electrode patterns, according to specific applications.

For example, FIG. 3 shows electrodes 11-15a arranged in quadrants. FIG. 4 shows a crossed shape, where the electrode patterns are symmetric with respect to a central, crossed electrode, which can serve as a reference electrode, for example. FIG. 5 depicts concentric electrode shapes, having radial symmetry (in-plane), which can advantageously be used in applications where radially symmetric pressure need be applied to the microneedles 16, for example. The interdigitated pattern of FIG. 6 allows a large area (in-plane) of interaction between the electrodes, which are suitable for impedance/conductance measurements, for example. More generally, the pattern can adapted, given an available area, so as to match impedance/conductance measurement needs.

Note, the orientation of the apertures 18 and perpendicular facets 16p may possibly vary from one needle to the other, or from one portion of the surface to the other, contrary to the depictions of FIGS. 3-6. I.e., needles and apertures 18 need not systematically be identically oriented.

In the example of FIG. 3, the complementary portions on which electrodes are patterned are arranged in distinct sectors of the base surface S of the structured substrate. I.e., outer peripheries of such complementary portions form quadrants. More generally, the outer limits of the sectors may form any 2D convex shape.

As further seen in FIGS. 2, 7 and 11, 12, the electrodes 11-15a may, in embodiments, further be structured so as to electrically connect opposite sides of the substrate 10. I.e., the electrode materials are arranged so as to connect the base surface S on one side to the opposite side of the substrate. For example, the electrically conductive material layers 71-75 used to form the electrodes may uninterruptedly coat the structured polymer substrate on contiguous sides thereof, so as to electrically connect the top side to the bottom side of the substrate, for reasons of ergonomics. That is, the structured side of the substrate 10 may be applied on a body to collect and analyze micro-quantities of fluids arising from the body, while readout electronics 3 (see FIG. 1) can be provided on the opposite side to read signals obtained from the electrodes 11-15a, in operation of the sensor device 1, as illustrated in FIGS. 1 and 7.

In detail, referring back to FIG. 1, the sensor device 1 may further include a readout electronic unit 3, 5, where the latter comprises a housing 5 and electronics 3 encapsulated in the housing 5. The electronics 3 and the housing 5 are configured such that the electronics 3 can be set in electric communication with the electrodes 11-15a, so as for the unit 3, 5 to read signals obtained from the electrodes 11-15a, in operation of the device 1. This electronic unit 3, 5 may also be designed as a peripheral device, which may for instance be removably connected to the sensing part 10 of the device 1. E.g., the housing 5 and/or the structured substrate 10 may accommodate a snap-fit mechanism to connect the electronics 3 to the electrodes 11-15a on the structured substrate 10. Thus, the present devices 1 may be provided as a kit of parts.

Referring more specifically to FIG. 7, another aspect of the invention is now discussed, which concerns a method of analysis of a fluid, using a sensor device 1 such as described above. Essentially, the sensing part of the device 1 (i.e., the structured polymer substrate 10) is first applied S200 onto a body 200 (e.g., onto human or animal skin, a food product or a drug, such as a gelling agent). Depending on the application, the microneedles 16 may or may not need to slightly penetrate into the body. Applying the substrate 10 onto the body allows a fluid produced by the body to contact an exposed surface of the electrodes 11-15a. Next, signals obtained from the electrodes 11-15a are read at S300, e.g., by an electronic unit 3, 5 and so as to collect data as to the body or a state thereof, as suggested in FIG. 7.

Figure 1:
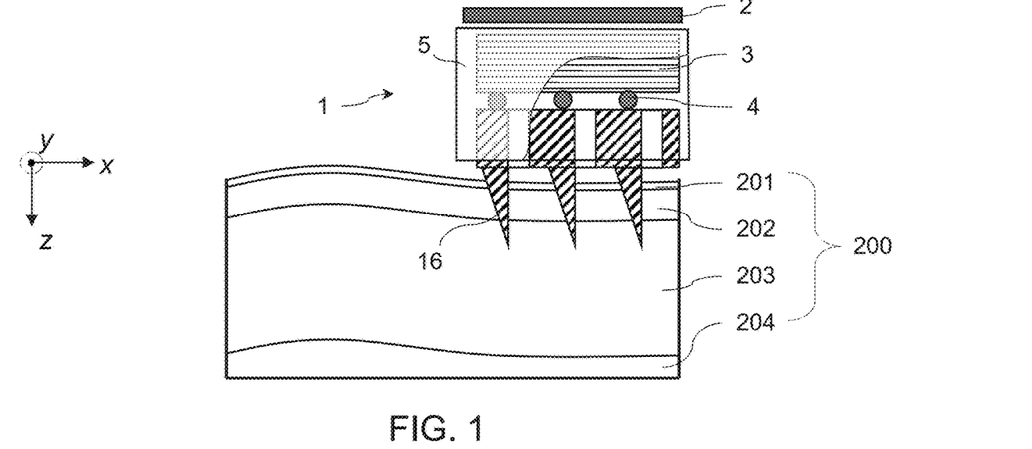
FIG. 1 is a 2D cross-sectional view of a sensor device, showing the device applied onto a body to probe interstitial fluids from this body, as in embodiments of the invention.

To illustrate further the readout principle, preferred embodiments are now described, in reference to FIG. 1, wherein a cross-section of a body part 200 is depicted, which represents human skin. It notably shows the dermis 203, i.e., a layer of skin between the epidermis 202 (below the stratum corneum 201) and subcutaneous tissues, including the epidermis 204. Here the sensing device 1 is assumed to comprise a sensing electrode, whose exposed surface consists of TiN, and a reference electrode, whose exposed surface is AgCl. Upon insertion into a medium 200 that comprises $H_3O^+$ ions, as is the case in the interstitial fluid present in the dermal region 203, a potential difference between the sensing electrode and the reference electrode can be sensed, which is related to the activity of $H_3O^+$ ions in the medium via the Nernst equation. The readout unit 3, 5 that is electrically connected to the electrodes may, in this example, comprise a high-impedance voltmeter as well as data acquisition and logic units, which, in combination, provide means to record voltage signals as a function of time.

Further signal processing electronics may be included (or remotely connected to the readout unit 3, 5) for filtering, amplification and transformation of the signals measured, if needed. Communication protocols such as the so-called I2C or UART protocol may be implemented for data communication within the readout unit 3, 5 and in a bus connecting the readout unit 3, 5 to further computing systems. If needed, the readout unit 3, 5 may further comprise a wireless communication unit to transfer the data, e.g., thanks to any suitable wireless communication standard, to said computing systems.

In embodiments, the sensing electrode and reference electrode may have exposed surfaces made of the same material, for example gold, in which case the potential difference between them is expected to be zero. A current may nonetheless be applied to these electrodes by means of an external circuit (e.g., forming part of the electronics 3), such that the magnitude of current will sinusoidally vary over time, so as to generate a sinusoidally varying voltage across the two electrodes. There, the relationship between the transient voltage and current patterns may be used to obtain an impedimetric sensor which is sensitive to the medium surrounding the two electrodes. For impedimetric sensing, the readout unit 3, 5 shall typically comprise a signal generator and an impedance bridge. As an alternative to the impedance bridge, a lock-in amplifier or frequency-response analyzer may be implemented in the readout unit 3, 5, for the purpose of performing impedimetric measurements. Just like in variants evoked above, the readout unit 3, 5 may further comprise additional units, e.g., a data acquisition unit, a logic unit, a signal processing unit, and a communication unit for the intended operation.

The biosensing applications contemplated herein are not limited to sensing in vivo. As mentioned earlier, the present device may also be used to sense properties of food products or, even, drug products or, still, to any material processed in vitro.

According to another aspect, the invention can further be embodied as methods of fabrication of a sensor device 1. Essentially, such a fabrication method revolves around patterning and structuring S10-S90 (FIG. 9) a polymer substrate 10 to form a set of microneedles 16 and a respective set of vias 17, as well as electrodes 11-15a, as described earlier in reference to FIGS. 1-8.

Figure 9:
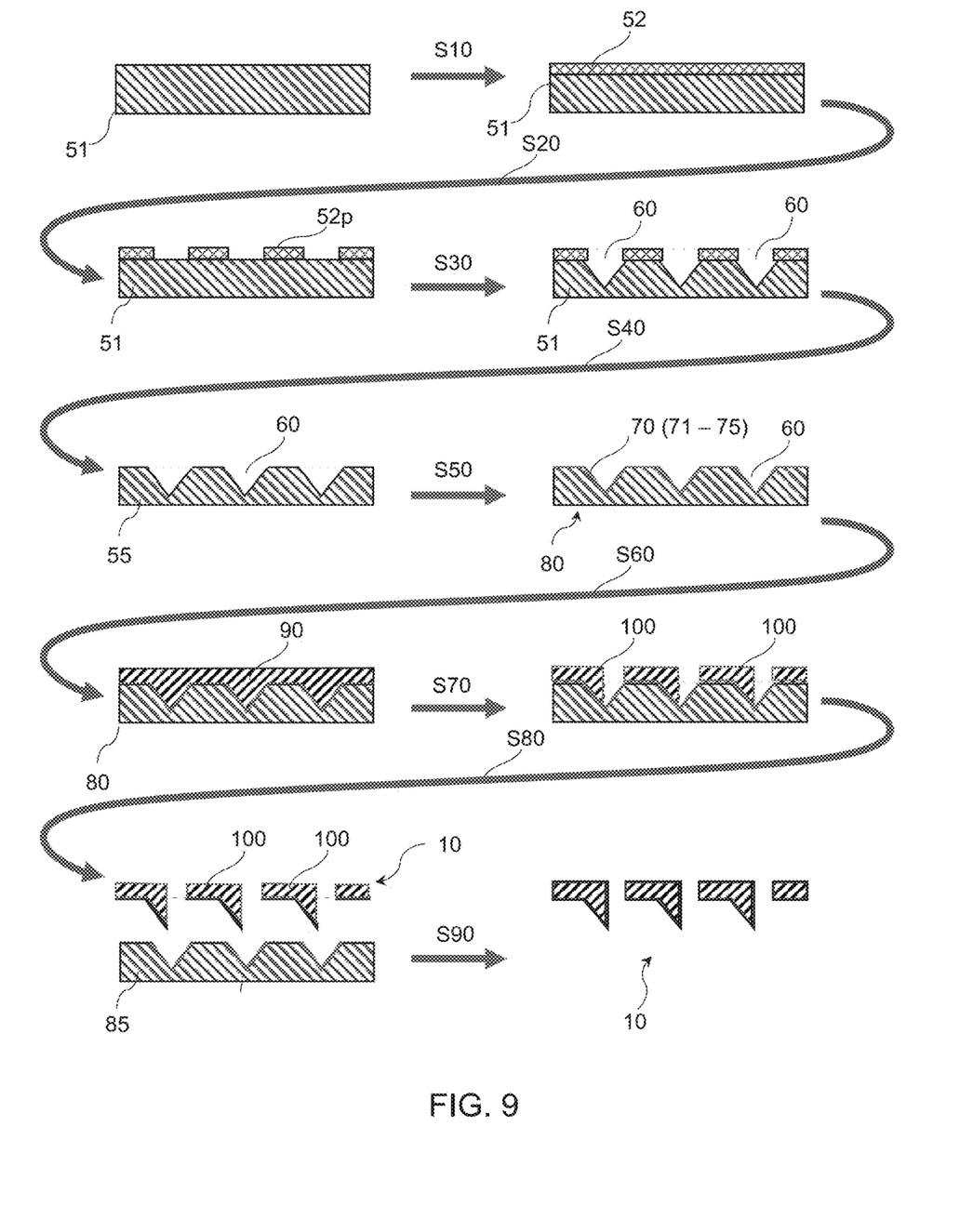
FIG. 9 is a sequence illustrating high-level fabrication steps of a sensor device, according to embodiments.

Referring to FIG. 9, a particularly interesting aspect of the invention concerns a method of fabrication, which relies on an inverse pattern. In such a method, electrically conductive material layers 11-15a are patterned S50 onto a sacrificial layer 73 that coats a mold 55 structured S10-S40 so as to form the desired inverse pattern.

A polymer substrate 90 is next complementarily patterned S60-S70 onto the electrically conductive material layers to form the set of microneedles 16, i.e., according to the inverse pattern previously obtained. The microneedles 16 accordingly formed extend from a base surface S of the substrate 90, which is exposed to the mold.

This polymer substrate is otherwise structured S70 so as to form a substrate 100 with a set of vias 17, wherein each via 17 extends through a thickness of the substrate 100, thereby forming a corresponding set of apertures 18 on the base surface S of the substrate 100. This is done so as for each of the apertures 18 to be adjacent to a respective one of the microneedles 16.

Finally, the sacrificial layer 73 is removed S80, which makes it possible to release S90 the substrate 100. This way, a structured substrate 10, 10a-10c can easily be obtained, as described earlier in reference to FIGS. 1-8.

As noted earlier, the electrode materials are preferably patterned S50 as a layer stack 70. The order of the layers 71-75 involved in the stack 70 patterned at step S50 makes sure that electrically conductive material layers 11-15a remain on the substrate upon releasing the latter by removing S80 the sacrificial layer 73. This way, a device 1 is obtained, which exhibits electrodes 11-15a formed by said material layers 11-15a, wherein such layers coat specific regions of the structured substrate 10, as explained earlier in reference to the present devices 1.

The vias 17 are preferably formed S70 by means of a photolithographic patterning process. For example, the polymer 100 may first be spin-coated S60 onto the mold 55, then baked (not shown), and then the vias 17 can be patterned S70 thanks to such a photolithographic process.

Figure 11:
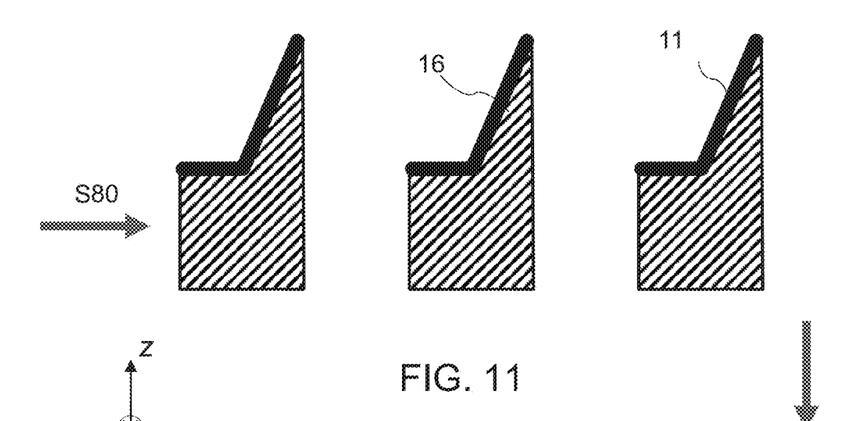
FIGS. 11 and 12 show 2D cross-sectional views of a polymer substrate, as obtained after steps S80 and S90 of FIG. 9, respectively.
Figure 12:
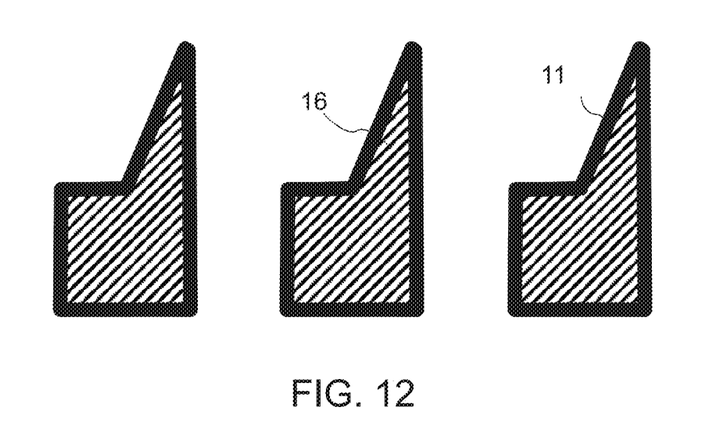

FIGS. 11 and 12 show 2D cross-sectional views of a polymer substrate, as obtained after steps S80 and S90 of FIG. 9, respectively. That is, after the patterning process S60-S70, the polymer substrate 90 is coated with electrodes on one side (FIG. 11). Then, a further backside coating (FIG. 12) allows the substrate to be coated on the opposite side too, if needed. This way, an electrode 11 can be patterned so as to electrically connect opposite sides of the substrate 10, as seen in FIG. 12.

Note that the mold 55 obtained at step S40 and then released 80 at step S80 can advantageously be re-used for a new cycle of steps S50-S90. Residual layers (e.g., Ti/Au) of materials will likely remain on the mold 80 after the release, for reasons explained below.

In embodiments, the fabrication method may further involve a series of initial steps (prior to patterning S50 the electrically conductive material layers 70), aiming at obtaining a mold 55, 80 structured according to the desired inverse pattern. Namely, an oxidized silicon substrate 51, 52 may first be obtained S10, which has an oxide layer 52 formed on top of the substrate 51, 52. Then, this oxide layer 52 may be patterned S20 to form openings (through residual portions 52p of the oxide layer). Next, the silicon substrate 51 is etched S30 through the openings formed to obtain said inverse pattern, whereby cavities 60 are created, which are shaped complementarily to the microneedles 16 to be subsequently obtained. Finally, the residual portions 52p of the oxide layer 52 are removed S40 to obtain the structured mold 55, onto which the sacrificial layer 73 is deposited (e.g., as part of a metal stack 70).

Pre-patterning electrode materials on the mold, as explained above, allows for improved control on the final electrode positions; this further eases the fabrication of the devices 1, inasmuch as the structured mold can later be reused.

For example, a 2 μm $SiO_2$ thermal substrate 10 may first be obtained S10 by growing a silicon oxide layer $SiO_2$ on a silicon (Si) surface, via a dry or wet oxidation process. Then, an inductively coupled plasma (ICP) etch step S20 is relied on to pattern the top oxide layer 52 and thereby form the hard mask 52p that comprises openings. Next, a KOH etch step S30 through the openings allows cavities 60 to be defined within the bulk Si substrate 10, which draws an inverse pattern for the needles. The structured Si substrate 55 will subsequently serve as a mold 55 for structuring the polymer substrate 10. Finally, after having removed S40 residual portions 52p of the hard mask, the sacrificial layer 73 is deposited S50 (e.g., which comprises chromium, as part of a metal layer stack 70) and a shadow mask is used to pattern S50 the electrode materials at selected places on the sacrificial layer 73.

In preferred embodiments, the deposited metal stack includes chromium 73 (50 nm), gold 74 (100 nm) and titanium 75 (10 nm), deposited in that order onto the silicon mold 55, whereby a pre-patterned mold 80 is obtained. The Cr/Au/Ti sequence of layers may for instance be successively deposited on residual Ti/Au dual layer of a mold 85, as obtained from a previous cycle S10-S90 (i.e., when re-using a mold 85). After deposition S60 and patterning S70 of the polymer substrate 90, the etching S80 of chrome 73 makes it possible to easily release S90 the polymer structure 100 along with the gold and titanium metallization layers 74, 75, where the gold layer forms the exposed surface. The titanium layer serving to promote the adhesion between gold 74 and the polymer 100. Instead of gold, other metals may include platinum or silver, as noted earlier. The metals may be further treated, for example by electrochemical or thermal oxidation or chemical chlorination, in order to obtain other sensing materials of interest. Further materials such as ceramics or polymers may further be used in the fabrication process S10-S90 or after release S90 of the polymer, as evoked earlier too.

Figure 10:
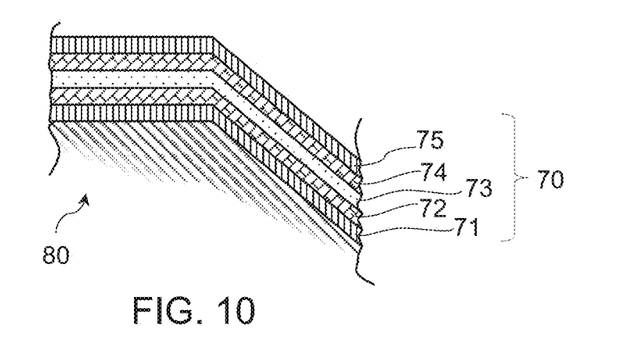
FIG. 10 is a magnified portion of the 2D cross-sectional view of a mold, as obtained after step S50 of FIG. 9, onto which electrode materials have been patterned as a metal layer stack, as in preferred fabrication methods.

When processing a mold 55, 80 for the first time, a metal stack Ti/Au/Cr/Au/Ti, respectively denoted by reference numerals 71-75 in FIG. 10, is successively deposited S50 on a structured mold 55. The subsequent etching S80 of chrome 73 makes it possible to release S90 the polymer structure 100 along with Au/Ti layers 74, 75 thereon, while a residual Ti/Au dual layer 71, 72 remains on the mold 85, which can be re-used for a next cycle, as noted above.

In preferred embodiments, step S70 may further comprise selectively exposing the polymer material to a suitable radiation source, so as to allow the needle sharpness to be increased, as Inventors observed. For example, a photosensitive polymer (e.g., SU-8) may first be spun coated onto the structured mold 80. Thereafter, the spun coated polymer structure 100 is placed in a vacuum oven at a slightly elevated temperature, e.g., 50° C., for a sufficient time, e.g., 1-2 hours, in order to remove air trapped inside the mold. The coated mold accordingly obtained is then removed from the vacuum oven and heated to 95° C. for at least 10 hours in order to complete a so-called soft bake step, which removes some solvent and increases the viscosity of the polymer. The polymer coating is then exposed to an ultraviolet (UV) light source through a mask that defines a pattern of portions of the polymer to be removed, according to a recommended exposure dose for the particular polymer. Following exposure, a hard bake step of the polymer is completed, for example by heating the coated mold to 95° C. with a dwell time of 15 minutes at that temperature. Following all exposure and thermal treatment steps, the coated mold is finally placed in a developer liquid (e.g., SU-8 propylene glycol methyl ether acetate, or PGMEA, for SU-8) in order to remove undesirable portions of polymer in the final device structure. As is understood by those skilled in the art, the temperatures and durations described in the above example may be adjusted according to the properties of the particular polymer used (e.g., chemical composition, thickness, etc.). Once all undesired portions of the polymer have been removed, the coated mold is immersed in a Cr etchant liquid and allowed sufficient time for the Cr etch step S80 to release the polymer substrate 100. Prior to S80, it may be beneficial to increase the hydrophilicity of the polymer coating by applying a brief plasma ashing step to the coated mold (not shown).

In particularly advantageous embodiments, the steps S10-S90 may be performed 24 on a wafer scale. I.e., assuming a properly structured, wafer-sized mold 55 is available, the steps of patterning S50 the material layers 11-15a, complementarily patterning S60-S70 the polymer substrate and removing S80 the sacrificial layer 73 can be implemented on a wafer scale. Then, after having removed S80 the sacrificial layer 73 to release S90 the wafer-scale polymer layer, the latter can be split to obtain several sensing parts. I.e., each of the parts eventually obtained comprises a structured polymer substrate portion 10 with respective electrodes 11-15a and sets of microneedles 16, vias 17 and apertures 18.

The polymer 100 may be for instance be split into parts by dicing it, after the release S90. As an alternative to dicing the polymer substrate 10, edges of single devices may be pre-defined during the patterning of the wafer-scale polymer substrate 10 (e.g., just like the vias 17). Thus, individual device parts 10 can be subsequently released upon removing the sacrificial layer and pre-defined, sacrificial edges, without further need for singulation. As another variants, pre-cut lines may be patterned, to subsequently ease the splitting e.g., by breaking the device parts by hand.

While the present invention has been described with reference to a limited number of embodiments, variants and the accompanying drawings, it will be understood by those skilled in the art that various changes may be made and equivalents may be substituted without departing from the scope of the present invention. In particular, a feature (device-like or method-like) recited in a given embodiment, variant or shown in a drawing may be combined with or replace another feature in another embodiment, variant or drawing, without departing from the scope of the present invention. Various combinations of the features described in respect of any of the above embodiments or variants may accordingly be contemplated, that remain within the scope of the appended claims. In addition, many minor modifications may be made to adapt a particular situation or material to the teachings of the present invention without departing from its scope. Therefore, it is intended that the present invention not be limited to the particular embodiments disclosed, but that the present invention will include all embodiments falling within the scope of the appended claims. In addition, many other variants than explicitly touched above can be contemplated. For example, other materials than those explicitly cited may possibly be contemplated.

What is claimed is:

1. A method of fabrication of a sensor device, the method comprising:
    patterning and structuring a polymer substrate to form:
        a set of microneedles that extend, each, from a base surface of the substrate; and
        a set of vias extending, each, through a thickness of the substrate, thereby forming a corresponding set of apertures on said base surface, wherein each of the apertures is adjacent to a respective one of the microneedles; and
        two electrodes, including a sensing electrode and a reference electrode, each comprising an electrically conductive material layer that coats a region of the substrate, so as to coat at least some of the microneedles and neighboring portions of said base surface.

2. The method of claim 1, wherein the electrically conductive material layer is patterned as a layer stack.

3. The method of claim 1, wherein the vias are formed by a photolithographic patterning process.

4. The method of claim 1, further including coating opposite sides of the polymer substrate.

5. The method of claim 1, further including selectively exposing the polymer substrate to a radiation source to allow the microneedle sharpness to increase.

6. A method of fabrication of a sensor device, the method comprising:
    patterning electrically conductive material layers onto a sacrificial layer to form an inverse pattern;
    complementarily patterning a polymer substrate onto the electrically conductive material layers to form a set of microneedles according to the inverse pattern, whereby each of the microneedles extends from a base surface of the substrate, wherein the polymer substrate is structured so as to exhibit a set of vias that extend, each, through a thickness of the polymer substrate, thereby forming a corresponding set of apertures on said base surface, and wherein each of the apertures is adjacent to a respective one of the microneedles formed; and
    removing the sacrificial layer, to release the polymer substrate with the electrically conductive material layers formed thereon, to obtain a sensor device having electrodes formed by said material layers on at least some of the microneedles and neighboring portions of the base surface of the substrate.

7. The method of fabrication according to claim 6, wherein the method further comprises, prior to patterning the electrically conductive material layers:
    obtaining an oxidized silicon substrate with an oxide layer on top of the substrate;
    patterning the oxide layer to form openings through residual portions of the oxide layer;
    etching the silicon substrate through the openings formed to obtain said inverse pattern, whereby cavities are created, which are shaped complementarily to the microneedles to be subsequently obtained;
    removing said residual portions of the oxide layer to obtain the structured mold; and
    depositing the sacrificial layer on a structured mold.

8. The method of fabrication according to claim 6, wherein
    complementarily patterning the polymer substrate further comprises selectively exposing the polymer substrate to a radiation source.

9. The method of fabrication according to claim 6, wherein
    the steps of patterning the material layers, complementarily patterning the polymer substrate and removing the sacrificial layer are implemented on a wafer scale.

10. The method of fabrication according to claim 9, wherein the method further comprises, after removing the sacrificial layer:
    splitting the polymer substrate to obtain several sensor devices, each comprising a structured polymer substrate with respective electrodes and sets of microneedles, vias and apertures.

11. The method of fabrication according to claim 10, wherein the splitting the polymer substrate includes dicing the polymer substrate.

12. The method of fabrication according to claim 10, wherein edges of each of the several sensor devices are pre-defined during the patterning of the polymer substrate.

13. The method of fabrication according to claim 10, further including patterning pre-cut lines for splitting the polymer substrate.

14. A method of analysis of a fluid, the method comprising:
    providing a sensor device comprising:
        a polymer substrate structured so as to form:
            a set of microneedles that extend, each, from a base surface of the substrate; and
            a set of vias extending, each, through a thickness of the substrate, thereby forming a corresponding set of apertures on said base surface, wherein each of the apertures is adjacent to a respective one of the microneedles; and
        two electrodes, including a sensing electrode and a reference electrode, each comprising an electrically conductive material layer that coats a region of the substrate, so as to coat at least some of the microneedles and neighboring portions of said base surface,
    applying the polymer substrate on a body for the microneedles to penetrate into the body and to allow a fluid from the body to contact an exposed surface of the electrodes, and
    reading signals obtained from the electrodes.

* * * * *